United States Patent
De Ferra et al.

(10) Patent No.: US 7,078,533 B2
(45) Date of Patent: Jul. 18, 2006

(54) METHOD FOR THE RACEMIZATION OF ETODOLIC ACID

(75) Inventors: Lorenzo De Ferra, Patrica (IT); Elio Ullucci, Patrica (IT)

(73) Assignee: Chemi Spa, Milan (IT)

( * ) Notice: Subject to any disclaimer, the term of this patent is extended or adjusted under 35 U.S.C. 154(b) by 138 days.

(21) Appl. No.: 10/800,404

(22) Filed: Mar. 12, 2004

(65) Prior Publication Data

US 2005/0014953 A1   Jan. 20, 2005

(30) Foreign Application Priority Data

Jul. 18, 2003  (IT) .......................... MI2003A1471

(51) Int. Cl.
*C07D 491/52*   (2006.01)
(52) U.S. Cl. ..................................... 548/432
(58) Field of Classification Search .................. 548/432
See application file for complete search history.

(56) References Cited

U.S. PATENT DOCUMENTS 4,501,899 A    2/1985  Abraham et al.
4,520,203 A    5/1985  Abraham et al.
4,604,469 A *  8/1986  Demerson et al. .......... 548/432
5,578,734 A    11/1996 Vecchi
6,964,979 B1 * 11/2005 Gopalsamy et al. ........ 514/411

FOREIGN PATENT DOCUMENTS

WO   WO 95/27713       10/1995
WO   WO 01/06990 A2    2/2001

OTHER PUBLICATIONS

Demerson et al., J Med Chem 1983, 26, 1778-80.
Lee et al., J Pharm Sci 1988, 77, 81-86.
Woods et al., Org Process Res Devel 2000, 4, 418-26.
Costa et al., Synthetic Comm 1996, 26, 3671-76.
Brenna et al., Tetrahedron 1997, 53, 17769-80.

* cited by examiner

*Primary Examiner*—Kamal A. Saeed
(74) *Attorney, Agent, or Firm*—Darby & Darby

(57) ABSTRACT

A method for the resolution of etodolic acid by crystallization of its salt with optically active 1-phenylethylamine and subsequent recovery of the (R,S) etodolic acid from the mother liquors of crystallization by racemization and crystallization is described.

13 Claims, No Drawings

METHOD FOR THE RACEMIZATION OF ETODOLIC ACID

The present invention relates to the resolution of etodolic acid by crystallization of its salt with optically active 1-phenylethylamine and subsequent recovery of the (R,S) etodolic acid from the mother liquors of crystallization by racemization and crystallization.

PRIOR ART

Etodolic acid, which can be defined chemically as 1,8-diethyl-1,3,4,9-tetrahydropyran[3,4-b]indol-1-acetic acid has the following structural formula:

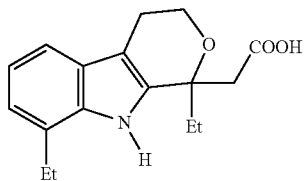

The product, which is commercially available as an anti-inflammatory agent, is the racemic mixture, although it is known that the anti-inflammatory activity is mainly in the S(+) isomer of etodolic acid, as described by C. A. Demerson and coll. in *J. Med. Chem.* 26, 1778, (1983).

The R(−) enantiomer, which has slight anti-inflammatory activity, on the other hand, can be used in combination with chemotherapy agents in the treatment of some types of cancer, as described in International patent application WO 01/06990.

The benefits of defining a process for isolating the two enantiomers by means of a simple and industrially sound method are therefore clear.

Over the years, various methods have been proposed for obtaining the S(+) dextrorotatory isomer from the racemic mixture with the use of various resolving agents; in particular, United States patent U.S. Pat. No. 4,501,899 provides for the use of cholesteryl aniline, United States patent U.S. Pat. No. 4,520,203 provides for the use of cinchonine, and United States patent U.S. Pat. No. 5,578,734 provides for the use of R-(+)-phenethylamine.

The resolution methods described are effective but have disadvantages, particularly with regard to yields and operating costs. In particular, one of the most uneconomic aspects is connected with the fact that the resolution of one of the two enantiomers leads to the formation of a racemic mixture which is enriched in the other enantiomer, and which is not normally recycled in the resolution process; in fact, for this to be possible, the "enriched" mixture must be racemized beforehand, but this cannot be achieved by the methods that have been known in the art up to now since etodolic acid does not racemize in a basic environment and degrades in an acid environment.

For example, in International patent application WO 95/27713 it is reported that, in conditions for the catalyzed acid racemization of etodolic acid, extensive decomposition of the product takes place. This is not surprising since its instability in an acid environment is known, as described by Lee et al., J. Pharm. Sci., (1988) 77 (1):81–86. This problem is overcome, also in WO 95/27713, by racemization of the product in ester form by treatment with protic acids or acid resins in various organic solvents. According to this method, fairly long reaction times (3 days) are required but, above all, transformation of etodolic acid into ester and subsequent hydrolysis are required.

Another method is described by Martin Woods in Organic Process Research & Development 2000, 4, 418–426, in which free etodolic acid is esterified with TMOA/toluene and racemized by addition of sulphuric acid and methanol; in this case also, the product obtained must then be hydrolyzed to obtain the racemic etodolic in acid form again.

For this reason, alternative methods of obtaining the optically active isomers of etodolic acid have been investigated.

The methods proposed provide for the total synthesis of S-(+)-etodolic acid by asymmetric Friedel-Crafts, as described by Paulo R. R. Costa et al., in Synthetic Communications, 26(19), 3671–3676 (1996), or by enzymatic reaction as described by Elisabetta Brenna et al in Tetrahedron, Vol. 53. No. 52, pp. 17769–17780, 1997.

However, given the complexity of the syntheses and the cost of the raw materials used, the techniques described are not sound as alternatives to resolution. There is therefore clearly a need to find a method of recycling the etodolic acid that is present in the mother liquors of the resolution in order to increase the overall yield of the isolation of optically active etodolic acid, without introducing additional synthesis steps.

DESCRIPTION OF THE INVENTION

The main object of the present invention is to identify the conditions for the recovery of racemic etodolic acid as part of the process for its resolution. This object is achieved with high yields and enables a product of high purity to be obtained with the use of low-cost raw materials and a simple method. With the method of the present invention, the racemization can in fact unexpectedly be carried out directly on the etodolic acid and therefore without the need to convert it into esters and, above all, without decomposition being observed.

The racemization reaction is performed either on the pure enantiomer or on the substrate enriched in one isomer, without particular differences.

It has in fact been found that the racemization of etodolic acid can be performed with quantitative yields and without any degradation in the presence of a catalyst selected from the Lewis acids, preferably in the presence of $SnCl_4$.

The subject of the present invention is therefore represented by a method of producing enantiomerically pure etodolic acid comprising: (i) the resolution of a racemic mixture of etodolic acid; (ii) the racemization of the etodolic acid remaining in the mother liquors in the presence of a Lewis acid, and (iii) the resolution of the racemic mixture thus obtained.

The resolution of the racemic mixture is performed by precipitation of an optically active salt of the enantiomer of interest with the use of the conventional methods described, for example, in U.S. Pat. No. 4,501,899, U.S. Pat. No. 4,520,203, and U.S. Pat. No. 5,578,734 (which are incorporated herein by reference).

Once the optically active salt has been separated by filtration, the mother liquors are concentrated with consequent precipitation of the racemic mixture, enriched in the other enantiomer. This "enriched" mixture is then dissolved in the solvent that is used in the subsequent racemization reaction. The solvent is normally an aprotic, apolar, organic solvent, preferably a chlorinated solvent such as, for example, chloroform, $CH_2Cl_2$ and/or tetrachloroethane, $CH_2Cl_2$ being particularly preferred; alternatively, the reaction may be performed in a mixture constituted by the aprotic, apolar, organic solvent and an aprotic, polar, organic solvent such as, for example THF, a THF/$CH_2Cl_2$ mixture being particularly preferred. The mixture is preferably constituted by from about 5 to about 15 volumes of the aprotic, apolar, organic solvent per volume of aprotic, polar, organic solvent, even more preferably from 8 to 10 volumes of apolar solvent ($CH_2Cl_2$) per volume of polar solvent (THF).

The reaction is performed at a temperature of between 10° C. and 45° C., preferably about 20° C.; the concentration of etodolic acid in the solvent is high and may vary between 0.1 and 1 moles of acid per litre of solvent, preferably between 0.3 and 0.4 moles of acid per litre of solvent.

The amount of catalyst may vary between 1% and 20% molar, relative to the substrate, and is preferably of the order of 1.5% molar.

The racemic mixture thus obtained is then precipitated with the use of methods known in the art such as, for example, precipitation by addition of heptane, and is then resolved as described above. Naturally, the method according to the present invention may be repeated in several cycles to the extent that it leads to a quantitative recovery of the enantiomer of interest.

As will be clear from the following examples, which are intended as further clarification of the invention without in any way constituting a limitation thereof, the main advantages of this method are that:

the racemization is performed directly on the etodolic acid in acid form;
no decomposition products are observed in the method;
the racemic etodolic acid is obtained with a chemical purity >98%;
the yields are greater than 80%;
the racemization method is simple, inexpensive and industrially advantageous.

EXAMPLES

1) Resolution of the Racemic Mixture and Recovery of the S-(+)-Etodolic Acid from the Mother Liquors of the Resolution Process 1 kg of R,S-etodolic acid (3.48 moles) was dissolved in 5 liters of acetone. 445 ml of S-(−)-phenylethylamine (3.48 moles) was added dropwise and slight exothermy from 23° C. to 28° C. was observed; after the dropwise addition, the solution was heated to 35° C. and stirring was continued until precipitation was observed. The solution was cooled to 20° C. and stirring was continued for 20 hours. The solid was filtered out, taken up in 4 liters of ethyl acetate, and whisked with two 1500 ml portions of 4% hydrochloric acid, the organic phase was concentrated to a volume of 550 ml and taken up with 420 ml of heptane to bring about crystallization. 248 g of R-(−)-etodolic acid was obtained.

The solution was concentrated to a residual volume of 1.8 liters and was then taken up with 5.4 liters of heptane, causing the formation of abundant precipitate. The mixture was left for 3 hours with stirring at 20° C., the precipitate was filtered out and 880 g of etodolic acid salt was recovered. The solid was dissolved in 8 liters of AcOEt and two washings with 3 liters of 4% HCl and one with 3 liters of $H_2O$ were performed.

The organic phase was evaporated to a residual volume of 1.15 liters, 1.26 liters of heptane was added, the mixture was left at 20° C. for 3 hours with stirring, and the precipitate was filtered out. 545 g of S-(+)-etodolic acid was recovered by this method, with a 42% enantiomeric excess.

2. Racemization a) 10 g (34.8 mmoles) of S-(+)-etodolic acid (42% enantiomeric excess) was dissolved in 100 ml of $CH_2Cl_2$ at 20° C. 60 µl (0.52 mmoles) of $SnCl_4$ was added and the mixture was left for 2 hours with stirring. Two washings with 100 ml of $H_2O$ were performed, the organic phase was separated and was concentrated to a residual volume of 15 ml, 20 ml of heptane was added, and the mixture was left at 20° C. for 3 hours with stirring. The precipitate was filtered out and 8.1 g of racemic etodolic acid was thus recovered.

b) 10 g (34.8 mmoles) of S-(+)-etodolic acid (42% enantiomeric excess) was dissolved in 100 ml of $CH_2Cl_2$ at 20° C.

60 µl (0.52 mmoles) of $SnCl_4$ was added and the mixture was left for 2 hours with stirring. Two washings with 100 ml of $H_2O$ were performed and the organic phase was extracted with 40 ml of 6% NaOH. The aqueous phase was separated, diluted with 10 ml of MeOH and acidified to pH=5 with formic acid. The mixture was left at 0° C. for 1 hour with stirring and was filtered and 7.6 g of racemic etodolic acid was recovered.

c) 2 g (6.96 mmoles) of R-(−)-etodolic acid (98% enantiomeric excess) was dissolved in 18 ml of $CH_2Cl_2$ and 2 ml of THF at 20° C. 160 µl (1.39 mmoles) of $SnCl_4$ was added and was left under reflux for 4 hours with stirring. Two washings with 18 ml of $H_2O$ were performed, the organic phase was separated and was concentrated to a residual volume of 3 ml, 5 ml of heptane was added and the mixture was left at 20° C. for 3 hours. The precipitate was filtered out and 1.5 g of racemic etodolic acid was thus recovered.

The invention claimed is:

1. Method of producing enantiomerically pure etodolic acid comprising: (1) the resolution of a racemic mixture of etodolic acid; (ii) the racemization of the etodolic acid remaining in the mother liquors, in the presence of a Lewis acid, and (iii) the resolution of the racemic mixture thus obtained.

2. Method according to claim 1, characterized in that the Lewis acid is $SnCl_4$.

3. Method according to claim 1, characterized in that the racemization is performed in an aprotic, apolar, organic solvent.

4. Method according to claim 3, characterized in that the aprotic, apolar, organic solvent is a chlorinated solvent.

5. Method according to claim 4, characterized in that the chlorinated solvent is $CH_2Cl_2$.

6. Method according to claim 1, characterized in that the racemization is performed in a mixture constituted by an aprotic, apolar, organic solvent and an aprotic, polar, organic solvent.

7. Method according to claim 6, characterized in that the mixture is contituted by from about 5 to about 15 volumes of the aprotic, apolar, organic solvent per volume of aprotic, polar, organic solvent, preferably from 8 to 10 volumes.

8. Method according to claim 6, characterized in that it is performed in a mixture of THF and $CH_2Cl_2$.

9. Method according to claim 1, characterized in that the concentration of the etodolic acid is the solvent in the racemization step is between 0.1 and 1 moles of acid per litre of solvent, preferably between 0.3 and 0.4 moles.

10. Method according to claim 1, characterized in that the quantity of catalyst is between 1% and 20% molar, relative to the etodolic acid.

11. Method according to claim 10, characterized in that the quantity of catalyst is about 1% molar, relative to the etodolic acid.

12. Method according to claim 1, characterized in that the racemization is performed at a temperature of between 10 C and 45 C, preferably about 20 C.

13. Method according to claim 1, characterized in that the resolution of the racemic mixture is performed by precipitation of an optically active salt of the enantiomer of interest.

* * * * *